US009174201B2

(12) United States Patent
Ernst et al.

(10) Patent No.: US 9,174,201 B2
(45) Date of Patent: Nov. 3, 2015

(54) METHOD FOR THE CONTINUOUS PRODUCTION OF AN AMINE USING AN ALUMINUM—COPPER CATALYST

(75) Inventors: Martin Ernst, Heidelberg (DE); Bernd Stein, Alsbach-Hähnlein (DE); Steffen Maas, Bubenheim (DE); Jörg Pastre, Bensheim (DE); Thorsten Johann, Ludwigshafen (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 13 days.

(21) Appl. No.: 13/119,948

(22) PCT Filed: Sep. 9, 2009

(86) PCT No.: PCT/EP2009/061691
§ 371 (c)(1),
(2), (4) Date: Mar. 18, 2011

(87) PCT Pub. No.: WO2010/031719
PCT Pub. Date: Mar. 25, 2010

(65) Prior Publication Data
US 2011/0172430 A1 Jul. 14, 2011

(30) Foreign Application Priority Data

Sep. 19, 2008 (EP) .................................. 08164749

(51) Int. Cl.
| C07C 211/14 | (2006.01) |
| C07C 211/35 | (2006.01) |
| C07C 209/26 | (2006.01) |
| B01J 23/72 | (2006.01) |
| B01J 35/02 | (2006.01) |
| B01J 37/00 | (2006.01) |
| C07C 209/16 | (2006.01) |
| B01J 21/04 | (2006.01) |
| B01J 37/02 | (2006.01) |
| B01J 37/18 | (2006.01) |

(52) U.S. Cl.
CPC ................ B01J 23/72 (2013.01); B01J 35/023 (2013.01); B01J 37/0009 (2013.01); C07C 209/16 (2013.01); C07C 209/26 (2013.01); B01J 21/04 (2013.01); B01J 37/0201 (2013.01); B01J 37/18 (2013.01); C07C 2101/14 (2013.01)

(58) Field of Classification Search
CPC .. C07C 209/16; C07C 209/26; C07C 211/06; C07C 211/08; C07C 211/35; C07C 213/02; C07C 217/08
USPC .................... 564/472, 479; 546/184; 548/579
See application file for complete search history.

(56) References Cited

U.S. PATENT DOCUMENTS

| 3,275,554 | A | | 9/1966 | Wagenaar et al. |
| 3,751,475 | A | | 8/1973 | Van der Voort et al. |
| 4,062,899 | A | * | 12/1977 | Laurer et al. ................... 568/855 |
| 4,229,359 | A | | 10/1980 | Deluca et al. |
| 4,310,697 | A | | 1/1982 | Cheminal et al. |
| 4,739,051 | A | | 4/1988 | Schroeder et al. |
| 4,806,690 | A | | 2/1989 | Bowman |
| 4,832,702 | A | | 5/1989 | Kummer et al. |
| 4,845,218 | A | | 7/1989 | Schroeder |
| 4,910,304 | A | | 3/1990 | Fischer et al. |
| 4,922,023 | A | * | 5/1990 | Fischer et al. ................. 564/479 |
| 5,847,131 | A | | 12/1998 | Simon et al. |
| 6,111,100 | A | | 8/2000 | Riechers et al. |
| 6,187,957 | B1 | | 2/2001 | Meyer et al. |
| 6,448,457 | B1 | | 9/2002 | Hesse et al. |
| 6,817,957 | B2 | * | 11/2004 | Flaum et al. ................... 473/563 |
| 7,053,247 | B2 | | 5/2006 | Lif et al. |
| 7,405,327 | B2 | * | 7/2008 | Haese et al. ................... 564/472 |
| 7,615,665 | B2 | | 11/2009 | Gerlach et al. |
| 2004/0082821 | A1 | | 4/2004 | Koch et al. |

(Continued)

FOREIGN PATENT DOCUMENTS

| DE | 2125039 | | 12/1971 |
| DE | 2445303 | A1 | 4/1976 |

(Continued)

OTHER PUBLICATIONS

Liu et al. "Honeycomb ceramic . . . " CA142:416230 (2005).*
Dep. Energy "Clear coal technology" p. 1-24 (1999).*
Nanda et al. "Pharmaceutical Eng." p. 1-22 (2008).*
Standard Oli v Am. Cyanamid 224 USPQ 210, p. 1-13 (1984).*
Turner "High throughput . . . " Surface Sci. p. 1763-1769 (2009).*
Fischer et al. "Process for the preparation . . . " CA111:57047 (1989).*
Morbidelli et al. "Catalyst design" Chembridge series in chemical engineering p. 95-100, 119 (2001).*

(Continued)

Primary Examiner — Celia Chang
(74) Attorney, Agent, or Firm — Drinker Biddle & Reath LLP

(57) ABSTRACT

Process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a catalyst comprising copper oxide and aluminum oxide, wherein the reaction takes place in the gas phase and the catalytically active composition of the catalyst before reduction with hydrogen comprises
from 20 to 75% by weight of aluminum oxide ($Al_2O_3$),
from 20 to 75% by weight of oxygen-comprising compounds of copper, calculated as CuO,
from 0 to 2% by weight of oxygen-comprising compounds of sodium, calculated as $Na_2O$, and
less than 5% by weight of oxygen-comprising compounds of nickel, calculated as NiO, and the shaped catalyst body has a pellet shape having a diameter in the range from 1 to 4 mm and a height in the range from 1 to 4 mm.

12 Claims, No Drawings

(56) References Cited

U.S. PATENT DOCUMENTS

| | | |
|---|---|---|
| 2007/0157938 A1 | 7/2007 | Wolff |
| 2007/0232833 A1 | 10/2007 | Haese et al. |
| 2008/0221359 A1 | 9/2008 | Gerlach et al. |
| 2008/0255351 A1 | 10/2008 | Hoffer et al. |
| 2010/0274008 A1 | 10/2010 | Kubanek et al. |
| 2010/0274009 A1 | 10/2010 | Kubanek et al. |
| 2010/0274010 A1 | 10/2010 | Kubanek et al. |
| 2010/0274011 A1 | 10/2010 | Kubanek et al. |
| 2010/0274055 A1 | 10/2010 | Kubanek et al. |
| 2011/0054167 A1 | 3/2011 | Kubanek et al. |

FOREIGN PATENT DOCUMENTS

| | | |
|---|---|---|
| DE | 2844984 A1 | 4/1979 |
| DE | 3611230 | 10/1987 |
| DE | 19859776 A1 | 6/2000 |
| DE | 102005047464 A1 | 4/2007 |
| EP | 137478 | 4/1985 |
| EP | 227904 | 11/1985 |
| EP | 257443 | 8/1986 |
| EP | 0235651 A1 | 9/1987 |
| EP | 0261773 A1 | 3/1988 |
| EP | 440829 | 8/1991 |
| EP | 0514692 A2 | 11/1992 |
| EP | 599189 | 11/1992 |
| EP | 0589341 A1 | 3/1994 |
| EP | 673918 | 3/1994 |
| EP | 816350 | 6/1996 |
| EP | 1020455 | 1/1999 |
| EP | 1106600 | 12/1999 |
| EP | 1312599 | 10/2001 |
| EP | 1312600 | 10/2001 |
| GB | 1512797 A | 6/1978 |
| GB | 1585480 * | 3/1981 |
| JP | S54-63001 | 5/1979 |
| JP | H03258773 A | 11/1991 |
| JP | H07-278063 A | 10/1995 |
| JP | H11-244710 A | 9/1999 |
| JP | 2004-536866 A | 12/2004 |
| JP | 2007512010 A | 5/2007 |
| JP | 2007537177 A | 12/2007 |
| WO | WO-97/34694 A1 | 9/1997 |
| WO | WO-98/00383 A1 | 1/1998 |
| WO | WO 03/010125 A1 | 2/2003 |
| WO | WO 2005/110969 A1 | 11/2005 |
| WO | WO 2007/036496 | 4/2007 |
| WO | WO 2007/036498 | 4/2007 |
| WO | WO 2007/036499 A1 | 4/2007 |
| WO | WO-200703649 A1 | 4/2007 |
| WO | WO-2007036496 A1 | 4/2007 |
| WO | WO 2007/093514 | 8/2007 |
| WO | WO 2007/093552 | 8/2007 |
| WO | PCT/EP2008/067190 | 12/2008 |

OTHER PUBLICATIONS

Ostrovskii "An experience of catalyst design . . ." CI & CEQ 12(3) p. 187-194 (2005).*
Diethylene glyco, Wikipedia p. 1 (2013).*
International Search Report for PCT/EP2009/061691, mailing date Mar. 3, 2010.
International Preliminary Report for Patentability for PCT/EP2009/061691, dated Jul. 2009.
Perry's Chemical Engineers Handbook 7th Edition, "Catalysis", (1997), p. 29 of chapter 23.
Johnson Matthey Catalysts, "Commercial Information on the Catalyst PRICAT CZ 29/7 T" (2003).

* cited by examiner

METHOD FOR THE CONTINUOUS PRODUCTION OF AN AMINE USING AN ALUMINUM—COPPER CATALYST

CROSS-REFERENCE TO RELATED APPLICATIONS

This application is a national stage application (under 35 U.S.C. §371) of PCT/EP2009/061691, filed Sep. 9, 2009, which claims benefit of European application 08164749.7 filed Sep. 19, 2008, the contents of each of which are incorporated herein by reference in their entireties.

FIELD OF THE INVENTION

The present invention relates to a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a catalyst comprising copper oxide and aluminum oxide.

BACKGROUND

The process products are used, inter alia, as intermediates in the production of fuel additives (U.S. Pat. No. 3,275,554 A; DE 21 25 039 A and DE 36 11 230 A), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

EP 257 443 A (BASF AG) relates to a process for the preparation of trialkylamines (e.g. dimethylethylamine) by reaction of ammonium with alcohols in the presence of alkali metal hydroxide in the liquid phase over a catalyst comprising essentially only copper.

EP 227 904 A (BASF AG) teaches the preparation of dimethylethylamine or N,N-dimethylcyclohexylamine in the liquid phase by reaction of dimethylamine with cyclohexanol in the presence of alkali metal hydroxide and a catalyst which comprises essentially only copper as active metal or is a pure copper catalyst.

U.S. Pat. No. 4,910,304 A (BASF AG) discloses the preparation of N-methylpiperidine and N-methylmorpholine by reaction of pentanediol or diethylene glycol (DEG) with methylamine and 45% strength aqueous KOH solution over an all-active Cu/Al catalyst at 245° C. and 250 bar.

EP 137 478 A (BASF AG) relates to a process for preparing N-methylpiperidine or N-methylmorpholine by catalytic amination of pentanediol by means of methylamine in the gas phase at from 5 to 25 bar over a copper-comprising catalyst which has been obtained by heating a basic copper- and aluminum-comprising carbonate.

EP 235 651 A1 (BASF AG) teaches a process for preparing N-methylpiperazine from diethanolamine and methylamine over metal-comprising catalysts. The reaction is carried out in the liquid phase (downflow mode) (page 3, last paragraph). According to an example, a Cu/Al$_2$O$_3$ catalyst in pellet form, height=diameter=4 mm, is used.

EP 816 350 A (BASF AG) describes a process for preparing N-methylpiperidine and N-methylmorpholine by reaction of primary amine with a diol in the liquid or gas phase over a copper catalyst which has been obtained by impregnation of SiO$_2$ spheres with basic copper carbonate.

U.S. Pat. No. 4,739,051 A (BASF AG) teaches the preparation of morpholine and piperidine by reaction of DEG or pentanediol with ammonia under hydrogenation conditions in the gas phase at atmospheric pressure and 200° C. over an all-active Cu/Ni/Al catalyst in yields of 97 or 95%.

EP 514 692 A2 (BASF AG) discloses a process for preparing amines from alcohols in the presence of catalysts comprising copper and nickel and zirconium oxide and/or aluminum oxide.

EP 1 020 455 A (BASF AG) relates to a process for preparing bis(2-morpholinoethyl)ether by reaction of diethylene glycol (DEG) with ammonia under superatmospheric pressure and at elevated temperature in the presence of hydrogen and a copper-comprising hydrogenation catalyst.

EP 1 106 600 A (BASF AG) teaches the use of ZrO$_2$—Cu—Co—Ni catalysts in amination reactions. According to an example, 5×3 mm pellets are used as shaped catalyst bodies.

U.S. Pat. No. 4,806,690 A (Dow Chemical Comp.) relates to the amination of alcohols, aldehydes and ketones in the presence of a Co—Cu—Fe and Zn and/or Zr catalysts. In an example, 8-16 mesh catalyst particles are used.

DE 19 85 9776 A (BASF AG) relates to the preparation of amines by reaction of alcohols or aldehydes or ketones with amines over a catalyst which comprises copper and TiO$_2$ and to which metallic copper has been added prior to shaping of the catalyst material. According to an example, the catalyst is used as pellets having a diameter of 3 mm.

EP 440 829 A1 (U.S. Pat. No. 4,910,304) (BASF AG) describes the amination of diols over copper catalysts. The reaction is carried out in the liquid phase (downflow mode) (page 3, last paragraph). Suitable catalysts are the catalysts disclosed in DE 24 45 303 A (BASF AG) which can be obtained by heating a basic copper- and aluminum-comprising carbonate of the general composition Cu$_m$Al$_6$(CO$_3$)$_{0.5m}$O$_3$(OH)$_{m+12}$, where m is any, not necessarily integral, number from 2 to 6, for example the copper-comprising precipitated catalyst disclosed in loc. cit., example 1, which is prepared by treatment of a solution of copper nitrate and aluminum nitrate with sodium bicarbonate and subsequent washing, drying and heat treatment of the precipitate.

In the examples of EP 440 829 A, the catalyst is used as cylindrical shaped bodies having a length of 3 mm and a diameter of 3 mm.

WO 07/036,496 A1 (BASF AG) describes the reaction of diethylene glycol with ammonia in the presence of Cu—Ni—Co catalysts. The shaped catalyst body has, in the case of a pellet shape, a height of <3 mm.

WO 07/036,498 A1 (BASF AG) relates to the reaction of monoethanolamine with ammonia in the presence of Cu—Ni—Co catalysts. The shaped catalyst body has, in the case of a pellet shape, a height of <3 mm.

WO 07/093,514 A1 and WO 07/093,552 A1 (both BASF AG) teach the reaction of monoethylene glycol with ammonia in the presence of Ru—Co catalysts. The shaped catalyst body has, in the case of a pellet shape, a height of <3 mm.

WO 05/110969 A1 (BASF AG) describes a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a copper-comprising catalyst, with the catalytically active composition of the catalyst before reduction with hydrogen comprising from 20 to 85% by weight of aluminum oxide (Al$_2$O$_3$), zirconium dioxide (ZrO$_2$), titanium dioxide (TiO$_2$) and/or silicon dioxide ($SiO_2$) and the reaction being carried out isothermally in the gas phase in a tube reactor.

BRIEF SUMMARY

It was an object of the present invention to discover an improved economical process for the preparation of an amine. In particular, the process should make better yields, space-time yields (STYs) and selectivities possible.

[Space-time yields are given in "amount of product/(catalyst volume·time)" ($kg/(l_{cat}·h)$) and/or "amount of product/(reactor volume·time)" ($kg/(l_{reactor}·h)$)].

We have accordingly found a process for the continuous preparation of an amine by reaction of a primary or secondary alcohol, aldehyde and/or ketone with hydrogen and a nitrogen compound selected from the group consisting of ammonia, primary and secondary amines at a temperature in the range from 60 to 300° C. in the presence of a catalyst comprising copper oxide and aluminum oxide, wherein the reaction takes place in the gas phase and the catalytically active composition of the catalyst before reduction with hydrogen comprises
from 20 to 75% by weight of aluminum oxide ($Al_2O_3$),
from 20 to 75% by weight of oxygen-comprising compounds of copper, calculated as CuO,
from 0 to 2% by weight of oxygen-comprising compounds of sodium, calculated as $Na_2O$, and
less than 5% by weight of oxygen-comprising compounds of nickel, calculated as NiO, and the shaped catalyst body has a pellet shape having a diameter in the range from 1 to 4 mm and a height in the range from 1 to 4 mm.

DETAILED DESCRIPTION OF THE PREFERRED EMBODIMENTS

According to the invention, the advantageous combination of the specific catalyst having specific dimensions of the shaped catalyst body with a preferred isothermal mode of operation (amination of the starting material(s) mentioned) in gas-phase amination was recognized.

In the process of the invention, higher space-time yields compared to, for example, 5×5 mm pellets are achieved and the reaction selectivity is improved, because, inter alia, fewer scrambling products, i.e. by-products formed by intramolecular or intermolecular transfer of alkyl groups (e.g. disproportionation of alkylamine, e.g. DMA to form TMA, MMA, DMA; cf. example 1).

In addition, a greater catalyst activity, i.e. a higher space velocity over the catalyst, compared to, for example, 5×5 mm pellets is achieved at least equal yields and the reactor temperature can advantageously be set to a comparatively low value at least equal yields in the process of the invention.

Overall, making the catalyst geometry smaller in the process of the invention achieves a significant increase in efficiency in the production of amination products from aldehydes, ketones and alcohols in the gas phase.

The shaped catalyst body preferably has a pellet shape having a diameter in the range from 1.1 to 3.5 mm and a height in the range from 1.1 to 3.5 mm.

The shaped catalyst body particularly preferably has a pellet shape having a diameter in the range from 1.2 to 3.2 mm, in particular from 1.3 to 2.8 mm, more particularly from 1.4 to 2.5 mm, and a height in the range from 1.2 to 3.2 mm, in particular from 1.3 to 2.8 mm, more particularly from 1.4 to 2.5 mm.

The ratio of diameter:height in the pellet-shaped catalyst body is very particularly preferably in the range from 0.7 to 2.0, in particular in the range from 0.8 to 1.5, more particularly in the range from 0.9 to 1.2.

In the process of the invention, the catalysts are preferably used in the form of catalysts which consist entirely of catalytically active composition and, if appropriate, a shaping aid (e.g. graphite or stearic acid) if the catalyst is used as shaped body, i.e. comprise no further catalytically active accompanying substances.

In this context, the oxidic support material aluminum oxide ($Al_2O_3$) is regarded as part of the catalytically active composition.

To use the catalysts, it is possible to install the catalytically active composition in the reactor as shaped catalyst bodies, namely as pellets, after milling, mixing with shaping aids, shaping and heat treatment.

The concentrations (in % by weight) reported for the components of the catalyst are in each case based, unless indicated otherwise, on the catalytically active composition of the finished catalyst after its last heat treatment and before reduction with hydrogen.

The catalytically active composition of the catalyst after its last heat treatment and before reduction with hydrogen is defined as the sum of the catalytically active constituents and the abovementioned catalyst support material and comprises essentially the following constituents:
aluminum oxide ($Al_2O_3$) and oxygen-comprising compounds of copper and preferably oxygen-comprising compounds of sodium.

The sum of the abovementioned constituents of the catalytically active composition, calculated as $Al_2O_3$, CuO and $Na_2O$, is usually from 70 to 100% by weight, preferably from 80 to 100% by weight, particularly preferably from 90 to 100% by weight, more preferably from 98 to 100% by weight, more preferably ≥99% by weight, very particularly preferably 100% by weight.

The catalytically active composition of the catalysts used in the process of the invention can further comprise one or more elements (oxidation state 0) or their inorganic or organic compounds selected from among groups I A to VI A and I B to VII B and VIII of the Periodic Table.

Examples of such elements and compounds thereof are: transition metals such as Ni or NiO, Co or CoO, Re or rhenium oxides, Mn or $MnO_2$, Mo or molybdenum oxides, W or tungsten oxides, Ta or tantalum oxides, Nb or niobium oxides or niobium oxalate, V or vanadium oxides or vanadyl pyrophosphate; lanthanides such as Ce or $CeO_2$ or Pr or $Pr_2O_3$; alkali metal oxides such as $K_2O$; alkali metal carbonates such as $Na_2CO_3$; alkaline earth metal oxides such as CaO, SrO; alkaline earth metal carbonates such as $MgCO_3$, $CaCO_3$ and $BaCO_3$; boron oxide ($B_2O_3$).

The catalytically active composition of the catalysts used in the process of the invention comprises, after its last heat treatment and before reduction with hydrogen, from 20 to 75% by weight, preferably from 25 to 65% by weight, particularly preferably from 30 to 55% by weight, of aluminum oxide ($Al_2O_3$) and from 20 to 75% by weight, preferably from 30 to 70% by weight, particularly preferably from 40 to 65% by weight, very particularly preferably from 45 to 60% by weight, of oxygen-comprising compounds of copper, calculated as CuO, from 0 to 2% by weight, preferably from 0.05 to 1% by weight, particularly preferably from 0.1 to 0.5% by weight, of oxygen-comprising compounds of sodium, calculated as $Na_2O$,
less than 5% by weight, e.g. from 0.1 to 4% by weight, preferably less than 1% by weight, e.g. from 0 to 0.8% by weight, of oxygen-comprising compounds of nickel, calculated as NiO.

The catalytically active composition of the catalyst particularly preferably comprises, before reduction with hydrogen, less than 1% by weight, e.g. from 0 to 0.5% by weight, of oxygen-comprising compounds of cobalt, calculated as CoO.

The catalytically active composition of the catalyst used in the process of the invention very particularly preferably comprises no nickel, no cobalt and/or no ruthenium, in each case neither in metallic (oxidation state 0) form nor in ionic, in particular oxidized, form.

The oxygen-comprising compounds of copper are, in particular, copper(I) oxide and copper(II) oxide, preferably copper(II) oxide.

The catalytically active composition of the catalyst used in the process of the invention very particularly preferably comprises no zirconium dioxide ($ZrO_2$), titanium dioxide ($TiO_2$) and/or silicon dioxide ($SiO_2$).

In a particularly preferred embodiment, the catalytically active composition of the catalysts used in the process of the invention does not comprise any further catalytically active component, neither in elemental form nor in ionic form. In the particularly preferred embodiment, the catalytically active composition is not doped with further metals or metal compounds.

However, usual accompanying trace elements originating from the isolation of metallic Cu, possibly Ni, are preferably excepted therefrom.

Various methods of producing the catalysts used in the process of the invention are possible. They can be obtained, for example, by peptization of pulverulent mixtures of the hydroxides, carbonates, oxides and/or other salts of the components aluminum, copper, if appropriate sodium, with water and subsequent extrusion and heat treatment of the composition obtained in this way.

The catalysts used in the process of the invention can also be produced by impregnation of aluminum oxide ($Al_2O_3$) which may be present, for example, in the form of powder or pellets.

Aluminum oxide can here be used in various modifications, with preference being given to α-(alpha), γ-(gamma) or θ-$Al_2O_3$ (theta-$Al_2O_3$). Particular preference is given to using γ-$Al_2O_3$.

Aluminum oxide shaped bodies can be produced by customary methods.

Impregnation of the aluminum oxide is likewise carried out by customary methods, e.g. as described in EP 599 189 A, EP 673 918 A or A. B. Stiles, Catalyst Manufacture-Laboratory and, Commercial Preparations, Marcel Dekker, New York (1983), by application of an appropriate metal salt solution in one or more impregnation stages, using, for example, appropriate nitrates, acetates or chlorides as metal salts. After impregnation, the composition is dried and optionally calcined.

Impregnation can be carried out by the "incipient wetness" method, in which the inorganic oxide (i.e. aluminum oxide) is moistened with an amount of impregnation solution which is no more than that corresponding to its water uptake capacity. However, impregnation can also be carried out in an excess of solution.

In the case of multistage impregnation methods, it is advantageous to dry and if appropriate calcine the composition between individual impregnation steps. Multistage impregnation is particularly advantageous when a relatively large amount of metal is to be applied to the inorganic oxide.

To apply several metal components to the inorganic oxide, impregnation can be carried out simultaneously with, if appropriate, all metal salts or with, if appropriate, the individual metal salts in succession in any order.

Precipitation methods are preferably employed for producing the catalysts used in the process of the invention. Thus, they can be obtained, for example, by coprecipitation of the components from an aqueous salt solution by means of mineral bases in the presence of a slurry of a sparingly soluble, oxygen-comprising aluminum compound and subsequent washing, drying and calcination of the precipitate obtained. As sparingly soluble, oxygen-comprising aluminum compound, it is possible to use, for example, aluminum oxide. The slurries of the sparingly soluble aluminum compound can be produced by suspending fine powders of this compound in water with vigorous stirring. These slurries are advantageously obtained by precipitation of the sparingly soluble aluminum compound from aqueous aluminum salt solutions by means of mineral bases.

The catalysts used in the process of the invention are preferably produced by coprecipitation of all their components. For this purpose, it is advantageous to admix an aqueous salt solution comprising the catalyst components hot and while stirring with an aqueous mineral base, in particular an alkali metal base, for example sodium carbonate, sodium hydroxide, potassium carbonate or potassium hydroxide, until the precipitation is complete. The type of salts used is generally not critical: since the water-solubility of the salts is of primary importance in this procedure, a criterion is that they have the good solubility in water required for producing these relatively highly concentrated salt solutions. It is considered to be self-evident that when choosing the salts of the individual components, only salts having such anions which do not lead to interference, either by causing undesirable precipitation or by inhibiting or preventing the precipitation by complex formation, will naturally be chosen.

The precipitates obtained in these precipitation reactions are generally chemically nonuniform and comprise, inter alia, mixtures of the oxides, oxide hydrates, hydroxides, carbonates and insoluble and basic salts of the metal or metals used. To improve the filterability of the precipitates, it can prove to be advantageous for them to be aged, e.g. by leaving them to stand for some time after the precipitation, if appropriate hot or with passage of air.

The precipitates obtained after these precipitation processes are usually processed further to give the catalysts used according to the invention. After washing, they are preferably dried at from 80 to 200° C., more preferably from 100 to 150° C., and then calcined. Calcination is preferably carried out at temperatures in the range from 300 to 800° C., more preferably from 400 to 600° C., in particular from 450 to 550° C.

After calcination, the catalyst is advantageously conditioned, either by bringing it to a particular particle size by milling and/or by mixing it after milling with shaping aids such as graphite or stearic acid, pressing the mixture by means of a press to give the shaped bodies, namely pellets, and heat-treating these. The heat treatment temperatures preferably correspond to the temperatures in the calcination.

The catalysts produced in this way comprise the catalytically active metals in the form of a mixture of their oxygen-comprising compounds, i.e. in particular as oxides and mixed oxides.

The catalysts produced in this way are stored and, if appropriate, sold in this form. Before use as catalysts, they are usually prereduced. However, they can also be used without prereduction, in which case they are then reduced by the hydrogen present in the reactor under the conditions of the hydrogenative amination.

For the purposes of prereduction, the catalysts are firstly exposed to a nitrogen/hydrogen atmosphere at preferably from 150 to 200° C. for a period of, for example, from 12 to 20 hours and are subsequently treated in a hydrogen atmosphere at preferably from 200 to 400° C. for up to about 24 hours. In this prereduction, part of the oxygen-comprising metal compound(s) present in the catalysts is reduced to the corresponding metal(s), so that the latter are present together with the various oxygen compounds in the active form of the catalyst.

The reaction according to the process of the invention is preferably carried out in a tube reactor.

The reaction in the tube reactor according to the process of the invention is very particularly preferably carried out in the gas recycle mode.

The circulating gas, which comprises predominantly hydrogen, serves firstly to vaporize the starting materials and secondly as reactant for the amination reaction.

In the gas recycle mode, the starting materials (alcohol, aldehyde and/or ketone, hydrogen and the nitrogen compound) are preferably vaporized in a circulating gas stream and fed in gaseous form to the reactor.

The formative components (alcohol, aldehyde and/or ketone, the nitrogen compound) can also be vaporized as aqueous solutions and introduced together with the circulating gas stream into the catalyst bed.

Examples of suitable reactors having a circulating gas stream may be found in Ullmann's Encyclopedia of Industrial Chemistry, 5th Ed., Vol. B 4, pages 199-238, "Fixed-Bed Reactors". The reaction is very particularly preferably carried out in a shell-and-tube reactor or in a monostream plant.

In a monostream plant, the tube reactor in which the preferably isothermal reaction is carried out comprises a series arrangement of a plurality of (e.g. two or three) individual tube reactors.

The circulating gas flow is preferably in the range from 40 to 1500 m$^3$ (at operating pressure)/[m$^3$ of catalyst (bed volume)·h], in particular in the range from 100 to 700 m$^3$ (at operating pressure)/[m$^3$ of catalyst (bed volume)·h].

The circulating gas preferably comprises at least 10% by volume, in particular from 50 to 100% by volume, very particularly preferably from 80 to 100% by volume, of $H_2$.

The preferably isothermal reaction according to the process of the invention is preferably carried out with a temperature deviation of not more than +/−8° C., particularly preferably not more than +/−5° C., in particular not more than +/−4° C., very particularly preferably not more than +/−3° C., e.g. not more than +/−0 to +/−2° C. or not more than +/−0 to +/−1° C.

These temperature deviations relate to the respective temperatures in the respective catalyst bed, at the point at which the starting materials enter the catalyst bed and the point at which the reaction mixture leaves the catalyst bed.

It is possible for a plurality of catalyst beds to be connected in parallel or in series.

If a plurality of catalyst beds are connected in series, the abovementioned temperature deviations in the isothermal mode of operation which is preferred according to the invention relate to the respective temperature in the catalyst bed, at the point at which the starting materials enter the first catalyst bed and the point at which the reaction mixture leaves the last catalyst bed.

In a preferred embodiment, the temperature of the reactor tube is controlled from the outside by means of a stream of heat transfer medium which can be, for example, an oil, a salt melt or another heat-transferring liquid.

The way of carrying out the reaction according to the invention has, compared to a synthesis in the liquid phase and preferably compared to a nonisothermal synthesis in the gas phase, the advantages of, inter alia, better yields and greater safety in respect of runaway reactions, in particular at high reaction temperatures (e.g. from 200 to 300° C.).

The preferably isothermal gas-phase mode of operation greatly reduces the risk of a runaway reaction during the synthesis. The mass present in the reactor, which would be available for a runaway reaction, is only a fraction of the mass in a liquid-phase process.

The process of the invention is carried out continuously, with the catalyst preferably being arranged as a fixed bed in the reactor. Flow through the fixed bed of catalyst can be either from the top or from the bottom. The temperature, pressure and amount of the gas stream are set so that even relatively high-boiling reaction products remain in the gas phase.

The amine component (nitrogen compound) is preferably used in a from 0.90- to 100-fold molar amount, in particular in a from 1.0- to 10-fold molar amount, in each case based on the alcohol, aldehyde and/or ketone used.

The process of the invention is preferably carried out at an absolute pressure in the range from 1 to 300 bar, preferably from 1 to 50 bar, particularly preferably from 1 to 30 bar.

In the case of an amination of an alcohol, the process of the invention is preferably carried out at a temperature in the range from 80 to 300° C., preferably from 150 to 250° C., particularly preferably from 170 to 230° C.

In the case of an amination of an aldehyde and/or ketone, the process of the invention is preferably carried out at a temperature in the range from 60 to 200° C., preferably from 80 to 170° C., particularly preferably from 100 to 150° C.

The process is preferably operated with an amount of off-gas of from 5 to 800 standard cubic meters/h, in particular from 20 to 300 standard cubic meters/h.

[Standard cubic meters (standard m$^3$)=volume converted to STP].

In the process of the invention, the alcohol, aldehyde and/or ketone is preferably used as aqueous solution.

In the process of the invention, the ammonia, the primary or secondary amine is preferably used as aqueous solution.

The space velocity over the catalyst is preferably in the range from 0.1 to 2.0 kg, preferably from 0.1 to 1.0 kg, particularly preferably from 0.2 to 0.6 kg, of alcohol, aldehyde and/or ketone per liter of catalyst (bed volume) and hour.

The use of higher temperatures, higher total pressures and higher space velocities over the catalyst is possible. The pressure in the reactor, which is the sum of the partial pressures of the aminating agent, the alcohol, aldehyde and/or ketone component and the reaction products formed at the temperatures indicated, is advantageously increased to the desired reaction pressure by injection of hydrogen.

The water of reaction formed during the reaction generally does not have any adverse effect on the conversion, the reaction rate, the selectivity and the operating life of the catalyst and is therefore advantageously removed from the reaction product only in the work-up of the reaction product, e.g. by distillation.

The reaction product mixture is advantageously depressurized and the excess hydrogen and any excess aminating agent present are then removed and the crude reaction product obtained is purified, e.g. by means of fractional rectification. Suitable work-up methods are described, for example, in EP 1 312 600 A and EP 1 312 599 A (both BASF AG).

Unreacted starting materials and any suitable by-products obtained can be recirculated to the synthesis. After condensation of the products in a separator, unreacted starting materials can once again be passed, in discontinuous or continuous operation, in the circulating gas stream over the catalyst bed.

Primary and secondary amines which are, in addition to ammonia, suitable as aminating agents in the process of the invention are amines which owing to their boiling points can be kept in the gas phase under the process parameters employed in the process. The same applies to the process product amines and the starting materials for the process (alcohol, aldehyde, ketone).

The process of the invention makes it possible to prepare, for example, amines of the formula I

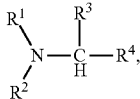

(I)

where
$R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $C_{3-30}$-dialkylaminoalkyl, aryl, aralkyl such as $C_{7-20}$-aralkyl or alkylaryl such as $C_{7-20}$-alkylaryl, or can together be $-(CH_2)_j-X-(CH_2)_k-$, $R^3$, $R^4$ are each hydrogen (H), alkyl such as $C_{1-20}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R^5-(OCR^6R^7CR^8R^9)_n-(OCR^6R^7)$, aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl or $Y-(CH_2)_m-NR^5-(CH_2)_q$ or can together be $-(CH_2)_l-X-(CH_2)_m-$ or $R^2$ and $R^4$ together are $-(CH_2)_l-X-(CH_2)_m-$, $R^5$, $R^{10}$ are each hydrogen (H), alkyl such as $C_{1-4}$-alkyl, alkylphenyl such as $C_{7-40}$-alkylphenyl, $R^6$, $R^7$, $R^8$, $R^9$ are each hydrogen (H), methyl or ethyl, X is $CH_2$, $CHR^5$, oxygen (O), sulfur (S) or $NR^5$, Y is $N(R^{10})_2$, hydroxy, $C_{2-20}$-alkylaminoalkyl or $C_{3-20}$-dialkylaminoalkyl, n is an integer from 1 to 30 and j, k, l, m, q are each an integer from 1 to 4.

The process of the invention is therefore preferably employed for preparing an amine I by reacting a primary or secondary alcohol of the formula II

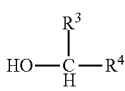

(II)

and/or aldehyde and/or ketone of the formula VI or VII

(VI)

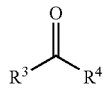

(VII)

with a nitrogen compound of the formula III

(III)

where $R^1$, $R^2$, $R^3$ and $R^4$ are as defined above.

The starting alcohol can also be an amino alcohol, e.g. an amino alcohol of the formula II.

As the definition of the radicals $R^2$ and $R^4$ indicate, the reaction can also occur intramolecularly in an appropriate amino alcohol, amino ketone or amino aldehyde.

To prepare the amine I, a hydrogen atom of the nitrogen compound III is purely formally replaced by the radical $R^4(R^3)CH$—with liberation of one molar equivalent of water.

The process of the invention is also preferably employed in the preparation of a cyclic amine of the formula IV

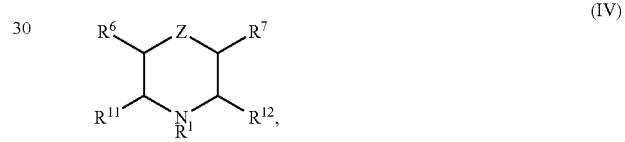

(IV)

where
$R^{11}$ and $R^{12}$ are each hydrogen (H), alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl or alkylaryl such as $C_7$-$C_{20}$-alkylaryl, Z is $CH_2$, $CHR^5$, oxygen (O), $NR^5$ or $NCH_2CH_2OH$ and $R^1$, $R^6$, $R^7$ are as defined above, by reaction of an alcohol of the formula V

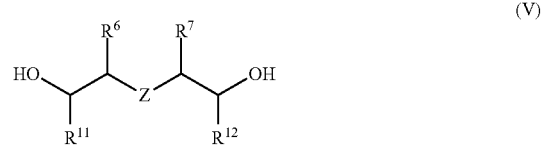

(V)

with ammonia or a primary amine of the formula VIII

(VIII)

The substituents $R^1$ to $R^{12}$, the variables X, Y, Z and the indices j, k, l, m, n and q in the compounds I, II, III, IV, V, VI, VII and VIII have, independently of one another, the following meanings:

$R^1$, $R^2$, $R^3$, $R^4$, $R^5$, $R^6$, $R^7$, $R^8$, $R^9$, $R^{10}$, $R^{11}$, $R^{12}$:
hydrogen (H), $R^3$, $R^4$:
alkyl such as $C_{1-20}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl or 3-n-butyl-n-nonyl, hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl or 1-(hydroxymethyl)ethyl, aminoalkyl such as $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl or N-(2-Aminoethyl)aminomethyl, hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl or 3-(2-hydroxyethylamino)propyl, $R^5$—$(OCR^6R^7CR^8R^9)_n$—$(OCR^6R^7)$, preferably $R^5$—$(OCHR^7CHR^9)_n$—$(OCR^6R^7)$, particularly preferably $R^5$—$(OCH_2CHR^9)_n$—$(OCR^6R^7)$, alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylaminoethyl, ethylaminomethyl, 2-ethylaminoethyl or 2-(isopropylamino)-ethyl, $(R^5)HN$—$(CH_2)_q$, $Y$—$(CH_2)_m$—$NR^5$—$(CH_2)_q$, heteroarylalkyl such as $C_{4-20}$-heteroarylalkyl such as pyrid-2-ylmethyl, furan-2-ylmethyl, pyrrol-3-ylmethyl or imidazol-2-ylmethyl, alkylheteroaryl such as $C_{4-20}$-alkylheteroaryl such as 2-methyl-3-pyridinyl, 4,5-dimethylimidazol-2-yl, 3-methyl-2-furanyl or 5-methyl-2-pyrazinyl, heteroaryl such as 2-pyridinyl, 3-pyridinyl, 4-pyridinyl, pyrazinyl, pyrrol-3-yl, imidazol-2-yl, 2-furanyl or 3-furanyl, $R^1, R^2, R^3, R^4$:

cycloalkyl such as $C_{3-12}$-cycloalkyl, preferably $C_{3-8}$-cycloalkyl such as cyclopropyl, cyclobutyl, cyclopentyl, cyclohexyl, cycloheptyl or cyclooctyl, particularly preferably cyclopentyl or cyclohexyl, alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxy-methyl, isopropoxymethyl, n-butoxymethyl, isobutoxymethyl, sec-butoxymethyl, tert-butoxymethyl, 1-methoxyethyl or 2-methoxyethyl, particularly preferably $C_{2-4}$-alkoxyalkyl, dialkylaminoalkyl such as $C_{3-30}$-dialkylaminoalkyl, preferably $C_{3-20}$-dialkylamino-alkyl, particularly preferably $C_{3-10}$-dialkylaminoalkyl such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl or 2-(N,N-diisopropylamino)ethyl, 3-(N,N-dimethylamino)propyl, $(R^5)_2N$—$(CH_2)_q$, aryl such as phenyl, 1-naphthyl, 2-naphthyl, 1-anthryl, 2-anthryl or 9-anthryl, preferably phenyl, 1-naphthyl or 2-naphthyl, particularly preferably phenyl, alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-tri-methylphenyl, 2-ethylphenyl, 3-ethylphenyl, 4-ethylphenyl, 2-n-propylphenyl, 3-n-propylphenyl or 4-n-propylphenyl, aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenyl-propyl, 2-phenylpropyl, 3-phenylpropyl, 1-phenylbutyl, 2-phenylbutyl, 3-phenyl-butyl or 4-phenylbutyl, particularly preferably benzyl, 1-phenethyl or 2-phenethyl, $R^3$ and $R^4$ together or $R^2$ and $R^4$ together a —$(CH_2)_j$—X—$(CH_2)_m$-group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^1, R^2$:

alkyl such as $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, particularly preferably $C_{1-4}$-alkyl, or $R^1$ and $R^2$ together a —$(CH_2)_j$—X—$(CH_2)_k$-group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^5, R^{10}$:

alkyl, preferably $C_{1-4}$-alkyl such as methyl, ethyl, n-propyl, isopropyl, n-butyl, isobutyl, sec-butyl or tert-butyl, preferably methyl or ethyl, particularly preferably methyl, alkylphenyl, preferably $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- or 3,5-didecylphenyl, in particular $C_{7-20}$-alkylphenyl, $R^6, R^7, R^8, R^9$:

methyl or ethyl, preferably methyl, $R^{11}, R^{12}$:

alkyl such as $C_1$-$C_{20}$-alkyl, cycloalkyl such as $C_3$-$C_{12}$-cycloalkyl, aryl, heteroaryl, aralkyl such as $C_7$-$C_{20}$-aralkyl or alkylaryl such as $C_7$-$C_{20}$-alkylaryl, in each case as defined above,

X:

$CH_2$, $CHR^5$, oxygen (O), sulfur (S) or $NR^5$, preferably $CH_2$ or O,

Y:

$N(R^{10})_2$, preferably $NH_2$ or $N(CH_3)_2$, hydroxy (OH), $C_{2-20}$-alkylaminoalkyl, preferably $C_{2-16}$-alkylaminoalkyl such as methylaminomethyl, 2-methylaminoethyl, ethylaminomethyl, 2-ethylaminoethyl or 2-(isopropylamino)ethyl, $C_{3-20}$-dialkylaminoalkyl, preferably $C_{3-16}$-dialkylaminoalkyl such as dimethylaminomethyl, 2-dimethylaminoethyl, 2-diethylaminoethyl, 2-(di-n-propylamino)ethyl or 2-(diisopropylamino)ethyl,

Z:

$CH_2$, $CHR^5$, O, $NR^5$ or $NCH_2CH_2OH$, j, l:

an integer from 1 to 4 (1, 2, 3 or 4), preferably 2 or 3, particularly preferably 2, k, m, q:
    an integer from 1 to 4 (1, 2, 3 or 4), preferably 2, 3 or 4, particularly preferably 2 or 3,
n:
    an integer from 1 to 30, preferably an integer from 1 to 8 (1, 2, 3, 4, 5, 6, 7 or 8), particularly an integer from 1 to 6.

Subject to the abovementioned provisos, suitable alcohols include virtually all primary and secondary alcohols having an aliphatic OH function. The alcohols can be linear, branched or cyclic. Both secondary alcohols and primary alcohols are aminated. The alcohols can also bear substituents or comprise functional groups which are inert under the conditions of the hydrogenative amination, for example alkoxy, alkenyloxy, alkylamino or dialkylamino groups, or may be hydrogenated under the conditions of the hydrogenative amination, for example C—C double or triple bonds. If polyhydric alcohols are to be aminated, it is possible for amino alcohols, cyclic amines or multiply aminated products to be obtained preferentially by means of control of the reaction conditions.

The amination of 1,4-diols leads, depending on the reaction conditions chosen, to 1-amino-4-hydroxy compounds, 1,4-diamino compounds or five-membered rings having a nitrogen atom (pyrrolidines).

The amination of 1,6-diols leads, depending on the reaction conditions chosen, to 1-amino-6-hydroxy compounds, 1,6-diamino compounds or seven-membered rings having a nitrogen atom (hexamethylenimines).

The amination of 1,5-diols leads, depending on the reaction conditions chosen, to 1-amino-5-hydroxy compounds, 1,5-diamino compounds or six-membered rings having a nitrogen atom (piperidines). Accordingly, amination of diglycol by means of $NH_3$ can give monoaminodiglycol (=ADG=$H_2N$—$CH_2CH_2$—O—$CH_2CH_2$—OH), diaminodiglycol or particularly preferably morpholine. In a corresponding fashion, diethanolamine particularly preferably gives piperazine. N-(2-Hydroxyethyl)piperazine can be obtained from triethanolamine.

Preference is given to aminating, for example, the following alcohols:
methanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)-ethanol, 2-(3,4-dimethoxyphenyl) ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine(1-amino-5-pentanol), n-hexanolamine(1-amino-6-hexanol), ethanolamine, diethanolamine, triethanolamine, N-alkyldiethanolamines, diisopropanolamine, 3-(2-hydroxyethylamino)propan-1-ol, 2-(N,N-dimethylamino) ethanol, 2-(N,N-diethylamino)ethanol, 2-(N,N-di-n-propylamino)-ethanol, 2-(N,N-diisopropylamino)ethanol, 2-(N,N-di-n-butylamino)ethanol, 2-(N,N-diisobutylamino) ethanol, 2-(N,N-di-sec-butylamino)ethanol, 2-(N,N-di-tert-butylamino)ethanol, 3-(N,N-dimethylamino)propanol, 3-(N,N-diethylamino)propanol, 3-(N,N-di-n-propylamino) propanol, 3-(N,N-diisopropylamino)propanol, 3-(N,N-di-n-butylamino)propanol, 3-(N,N-diisobutylamino)propanol, 3-(N,N-di-sec-butylamino)-propanol, 3-(N,N-di-tert-butylamino)propanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]-propane, methoxyethanol, propoxyethanol, butoxyethanol, polyisobutyl alcohols, polypropyl alcohols, polyethylene glycol ethers, polypropylene glycol ethers and polybutylene glycol ethers. The last-named polyalkylene glycol ethers are converted into the corresponding amines by transformation of their free hydroxyl groups in the reaction according to the invention.

Particularly preferred alcohols are methanol, ethanol, n-propanol, i-propanol, n-butanol, sec-butanol, 1,4-butanediol, 1,5-pentanediol, 1,6-hexanediol, 2-ethylhexanol, cyclohexanol, fatty alcohols, ethylene glycol, diethylene glycol (DEG), triethylene glycol (TEG), 2-(2-dimethylaminoethoxy)ethanol, N-methyldiethanolamine and 2-(2-dimethylaminoethoxy)ethanol.

Subject to the abovementioned provisos, ketones which can be used in the process of the invention include virtually all aliphatic and aromatic ketones. The aliphatic ketones can be linear, branched or cyclic, and the ketones can comprise heteroatoms. The ketones can also bear substituents or comprise functional groups which are inert under the conditions of the hydrogenative amination, for example alkoxy, alkenyloxy, alkylamino or dialkylamino groups, or may be hydrogenated under the conditions of the hydrogenative amination, for example C—C double or triple bonds. If polyfunctional ketones are to be aminated, it is possible to obtain amino ketones, amino alcohols, cyclic amines or multiply aminated products by means of control of the reaction conditions.

Preference is given to aminatively hydrogenating, for example, the following ketones:
acetone, ethyl methyl ketone, methyl vinyl ketone, isobutyl methyl ketone, butanone, 3-methyl-2-butanone, diethyl ketone, tetralone, acetophenone, p-methylacetophenone, p-methoxyacetophenone, m-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Subject to the abovementioned provisos, aldehydes which can be used in the process of the invention include virtually all aliphatic and aromatic aldehydes. The aliphatic aldehydes can be linear, branched or cyclic, and the aldehydes can comprise heteroatoms. The aldehydes can also bear substituents or comprise functional groups which are inert under the conditions of the hydrogenative amination, for example alkoxy, alkenyloxy, alkylamino or dialkylamino groups or may be hydrogenated under the conditions of the hydrogenative amination, for example C—C double or triple bonds. If polyfunctional aldehydes or keto aldehydes are to be aminated, it is possible to obtain amino alcohols, cyclic amines or multiply aminated products by means of control of the reaction conditions.

Preference is given to aminatively hydrogenating, for example, the following aldehydes:
formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and hydroformylated oligomers and polymers, e.g. hydroformylated polyisobutene (polyisobutenaldehyde) or the hydroformylation product of the oligomer obtained by methathesis of 1-pentene and cyclopentene.

As aminating agents in the hydrogenative amination of alcohols, aldehydes or ketones in the presence of hydrogen, it is possible to use either ammonia or primary or secondary, aliphatic or cycloaliphatic or aromatic amines.

When ammonia is used as aminating agent, the alcoholic hydroxyl group or the aldehyde group or the keto group is firstly converted into a primary amino group ($-NH_2$). The primary amine formed in this way can react with further alcohol or aldehyde or ketone to form the corresponding secondary amine and this can in turn react with further alcohol or aldehyde or ketone to form the corresponding, preferably symmetrical, tertiary amine. Depending on the composition of the reaction mixture or the feed stream (in a continuous mode of operation) and depending on the reaction conditions employed, viz. pressure, temperature, reaction time (space velocity over the catalyst), primary, secondary or tertiary amines can in this way be prepared preferentially as desired.

Cyclic amines such as pyrrolidines, piperidines, hexamethylenimines, piperazines and morpholines can be prepared in this way from polyhydric alcohols or dialdehydes or oligoaldehydes or diketones or oligoketones or ketoaldehydes by intramolecular hydrogenative amination.

Apart from ammonia, it is also possible to use primary or secondary amines as aminating agents.

These aminating agents are preferably used for preparing unsymmetrically substituted dialkylamines or trialkylamines, e.g. ethyldiisopropylamine and ethyldicyclohexylamine. For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared by the process of the invention are, for example, morpholine (from aminodiglycol), morpholine and/or bis(2-morpholinoethyl) ether (DMDEE) (from DEG and ammonia), 6-dimethylamino-1-hexanol (from hexanediol and dimethylamine (DMA)), triethylamine (from ethanol and diethylamine (DEA)), dimethylethylamine (from ethanol and DMA), N—($C_{1-4}$-alkyl)-morpholine (from DEG and mono($C_{1-4}$-alkyl)amine), N—($C_{1-4}$-alkyl)piperidine (from 1,5-pentanediol and mono($C_{1-4}$-alkyl)amine), piperazine (from aminoethylethanolamine (AEEA) and ammonia), N-methylpiperazine (from diethanolamine and MMA), N,N'-dimethylpiperazine (from N-methyldiethanolamine and MMA), ethylenediamine (EDA) and/or diethylenetriamine (DETA) and/or PIP (from monoethanolamine (MEOA) and ammonia), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino-4-aminopentane (from 1-diethylamino-4-hydroxypentane and $NH_3$), N,N-di ($C_{1-4}$-alkyl)cyclohexylamine (from cyclohexanone and/or cyclohexanol and di($C_{1-4}$-alkyl)amine), polyisobutenamine (from Pib oxo and $NH_3$), n-propylamines (such as mono-/dipropylamine, dimethylpropylamine) (from propionaldehyde and/or n-propanol and $NH_3$ or DMA), N,N-dimethyl-N-isopropylamine (from i-propanol and/or acetone and DMA), N,N-dimethyl-N-butylamines (1-butanol, 2-butanol or isobutanol and/or butanal, i-butanal or butanone and DMA), 2-(2-di($C_{1-4}$-alkyl)aminoethoxy)ethanol and/or bis (2-di($C_{1-4}$*alkyl)aminoethyl)ether (from DEG and di($C_{1-4}$-alkyl)amine), 1,2-ethylenediamine (EDA), diethylenetriamine (DETA) and/or piperazine (PIP) (from monoethylene glycol (MEG) and ammonia), 1,8-diamino-3,6-dioxaoctane and/or 1-amino-8-hydroxy-3,6-dioxaoctane (from triethylene glycol (TEG) and ammonia), 1-methoxy-2-propylamine (1-methoxyisopropylamine, MOIPA) (from 1-methoxy-2-propanol and ammonia).

EXAMPLES

The following examples were carried out using a copper catalyst having the composition 55% by weight of CuO and 45% by weight of gamma-$Al_2O_3$ (after its last heat treatment and before reduction with hydrogen).

The catalyst was produced by impregnation of gamma-$Al_2O_3$ powder with an aqueous copper nitrate solution. Tableting was carried out by the conventional method. Before commencement of the reaction, the catalyst was reduced in a stream of hydrogen at about 200° C. (see below).

The experiments were carried out continuously in gas-phase furnace reactors through which the reactants flowed from the bottom upward either in a 3.5 m long oil-heated double-walled tube which had an internal diameter of 4 cm and was filled from the bottom upward with 180 ml of ceramic spheres (6-9 mm), 1 liter of catalyst and 3.3 liters of inert material (V2A rings, 6 mm diameter) or in a 2.1 m long oil-heated double-walled tube which had an internal diameter of 4.11 cm and was filled from the bottom upward with 20 ml of ceramic spheres (6-9 mm), 1 liter of catalyst and 1.33 liters of inert material (V2A rings, 6 mm diameter). The reactors were operated at 20 and 25 bar, respectively.

The shaped catalyst bodies in pellet form were used in sizes of 5×5 mm (5 by 5 mm, i.e. 5 mm diameter and 5 mm height), 3×3 mm and 1.5×1.5 mm. After installation in the reactor, all catalysts were activated at atmospheric pressure according to the following method:

12 h at 180° C. (oil circuit reactor) with 20 standard l/h and 400 standard l/h of $N_2$, 12 h at 200° C. with 20 standard l/h of $H_2$ and 400 standard l/h of $N_2$, replace $N_2$ by 200 standard l/h of $H_2$ over 6 h, 6 h at 200° C. with 200 standard l/h of $H_2$. (standard l=standard liters=volume converted to STP).

The feed streams fresh hydrogen, circulating gas, pressurized gases and starting materials were heated to the desired reactor temperature by means of a system comprising three coil heat exchangers. The third heat exchanger was regulated via a temperature sensor just before the reactor. The oil heating of the double-wall reactor was likewise set to the desired reactor temperature. By means of two further coil heat exchangers, the reactor output was cooled firstly with river water and subsequently using a cryostat to 10° C. and fed to a pressure separator. The separation of liquid phase and gas phase occurred there. The liquid phase was depressurized in a low-pressure separator maintained at 30° C. from where the released gases were discharged via the offgas and the liquid was conveyed into the output drum. The gas phase from the pressure separator was recirculated in a defined amount via a circulating gas compressor and once again served as carrier gas for the starting materials. A pressure regulator ensured that excess gas was conveyed to the muffle furnace for incineration. Conversion and selectivity of the output were determined by gas-chromatographic analysis.

Example 1

The various shaped bodies were examined in the reaction of diethylene glycol (DEG) with dimethylamine (DMA) to form bis(dimethylaminoethyl)ether (BDMAE) at 210° C., a plant pressure of 20 bar, a WHSV of DEG of 0.5 kg/liter·h, a circulating gas flow of 10 standard m³/h and 300 standard l/h of fresh hydrogen.

(Standard m³=standard cubic meters=volume converted to STP).

It was observed that both conversion and selectivity of the amination reaction improved with the stepwise reduction in size of the shaped bodies from 5×5 mm via 3×3 mm to 1.5×1.5 mm. The conversion increased by up to 5% and the selectivity by up to 5% when comparing the 5×5 mm shaped bodies to the 1.5×1.5 mm shaped bodies. When the 1.5×1.5 mm shaped bodies were used, the content of BDMAE in the output from the synthesis could be improved by increasing the amount of DMA used from 29% by weight (5×5 mm) to over 40% by weight (1.5×1.5 mm) without a significant increase in interfering secondary components being observed. This means that the tendency for scrambling of DMA to monomethylamine (MMA) and trimethylamine (TMA), which occurs in the case of a corresponding increase in the proportion of DMA when using the 5×5 cm shaped bodies, was reduced.

Example 2

Shaped bodies having a size of 3×3 mm and 5×5 mm were examined in the reaction of butanediol with ammonia to form pyrrolidine at 240° C., a plant pressure of 20 bar and a WHSV of butanediol of 0.29 kg/liter·h. An increase in selectivity to the reaction product by 8% to 89% was observed when using the 3×3 mm shaped bodies compared to the 5×5 mm shaped bodies.

Example 3

Shaped bodies having a size of 3×3 mm and 5×5 mm were examined in the reaction of pentanediol with ammonia to form piperidine at 220-240° C., a plant pressure of 20 bar and a WHSV of pentanediol of 0.31 kg/liter·h. An increase in selectivity to the reaction product by more than 10% to about 92% was observed when using the 3×3 mm shaped bodies compared to the 5×5 mm shaped bodies.

Example 4

Shaped bodies having a size of 3×3 mm and 5×5 mm were examined in the reaction of propanal with dimethylamine to form N,N-dimethylpropylamine at 100° C., a plant pressure of 20 bar and a WHSV of 0.32 kg/liter·h. An increase in selectivity to the reaction product by 2% to 95% was observed when using the 3×3 mm shaped bodies compared to the 5×5 mm shaped bodies.

The invention claimed is:

1. A process for the continuous preparation of a product by reaction of a primary alcohol having an aliphatic OH function with hydrogen and a nitrogen compound, at an absolute pressure of from 1 to 30 bar and at a temperature in the range from 170 to 300° C. in the presence of a catalyst comprising copper oxide and aluminum oxide, wherein the reaction takes place in the gas phase and the catalytically active composition of the catalyst before reduction with hydrogen comprises from 25 to 65% by weight of aluminum oxide ($Al_2O_3$),
from 30 to 70% by weight of oxygen-comprising compounds of copper, calculated as CuO,
from 0 to 2% by weight of oxygen-comprising compounds of sodium, calculated as $Na_2O$, and
less than 1% by weight of oxygen-comprising compounds of nickel, calculated as NiO,
and the shaped catalyst body has a pellet shape having a diameter in the range from 1.3 to 2.8 mm and a height in the range from 1.2 to 3.2 mm, and
wherein the reaction is carried out in a tube reactor in a gas recycle mode in which the circulating gas flow is in the range from 40 to 1500 m³ (at operating pressure)/[m³ of catalyst (bed volume)×hours], and
wherein the product is 2-(2-di($C_{1-4}$-alkyl)aminoethoxy) ethanol, the primary alcohol having an aliphatic OH function is diethylene glycol, and the nitrogen compound is di($C_{1-4}$-alkyl)amine, or
wherein the product is bis(2-di($C_{1-4}$-alkyl)aminoethyl) ether, the primary alcohol having an aliphatic OH function is diethylene glycol, and the nitrogen compound is di($C_{1-4}$-alkyl)amine, or
wherein the product is bis(2-morpholinoethyl)ether (DMDEE), the primary alcohol having an aliphatic OH function is diethylene glycol, and the nitrogen compound is ammonia, or
wherein the product is dimethylethylamine (DMEA), the primary alcohol having an aliphatic OH functional is ethanol, and the nitrogen compound is dimethylamine (DMA).

2. The process according to claim 1, wherein the catalytically active composition of the catalyst before reduction with hydrogen further comprises less than 1% by weight of oxygen-comprising compounds of cobalt, calculated as CoO.

3. The process according to claim 1, wherein the catalytically active composition of the catalyst before reduction with hydrogen comprises from 0.05 to 1% by weight of oxygen-comprising compounds of sodium, calculated as $Na_2O$.

4. The process according to claim 1, wherein the catalytically active composition of the catalyst comprises no nickel, cobalt and/or ruthenium.

5. The process according to claim 1, wherein the reaction is carried out isothermally with a temperature deviation of not more than +/−8° C.

6. The process according to claim 1, wherein the reaction is carried out in a shell-and-tube reactor or in a monostream plant.

7. The process according to claim 1, wherein the temperature of the reactor tube or tubes is maintained from the outside by means of an oil stream or a salt melt.

8. The process according to claim 1, wherein the circulating gas comprises at least 10% by volume of hydrogen ($H_2$).

9. The process according to claim 1, wherein the amine component (nitrogen compound) is used in a from 0.90- to 100-fold molar amount based on the alcohol used.

10. The process according to claim 1, wherein the catalyst is arranged as a fixed bed in the reactor.

11. The process according to claim 1, wherein the alcohol is used as aqueous solution.

12. The process according to claim 1, wherein the ammonia or the primary or secondary amine is used as aqueous solution.

* * * * *